United States Patent [19]

Preston

[11] Patent Number: 5,705,711
[45] Date of Patent: Jan. 6, 1998

[54] MANUFACTURE OF METHYL TERTIARY BUTYL ETHER IN REACTIVE DISTILLATION COLUMN

[75] Inventor: Kyle Lee Preston, Port Arthur, Tex.

[73] Assignee: Huntsman Specialty Chemicals Corporation, Austin, Tex.

[21] Appl. No.: 516,228

[22] Filed: Aug. 17, 1995

[51] Int. Cl.⁶ ..................... C07C 41/00
[52] U.S. Cl. ............ 568/697; 568/698; 568/699
[58] Field of Search ................ 568/699, 687, 568/698

[56] References Cited

U.S. PATENT DOCUMENTS 5,243,091  9/1993  Kruse et al. ............... 568/697

*Primary Examiner*—Marianne M. Cintins
*Assistant Examiner*—Dwayne C. Jones
*Attorney, Agent, or Firm*—Russell R. Stolle; Ron D. Brown; Carl G. Ries

[57] ABSTRACT

Tertiary butyl alcohol and methanol are reacted in a primary reactor in the presence of an acid cation exchange resin to provide a primary reaction product comprising methyl tertiary butyl ether, unreacted tertiary butyl alcohol, unreacted methanol, isobutylene, water and oxygen-containing by-products, and the primary reaction product is charged to a reactive distillation column where additional methyl tertiary butyl ether is prepared from the methanol, tertiary butyl alcohol and isobutylene present in the primary reaction product.

8 Claims, 1 Drawing Sheet

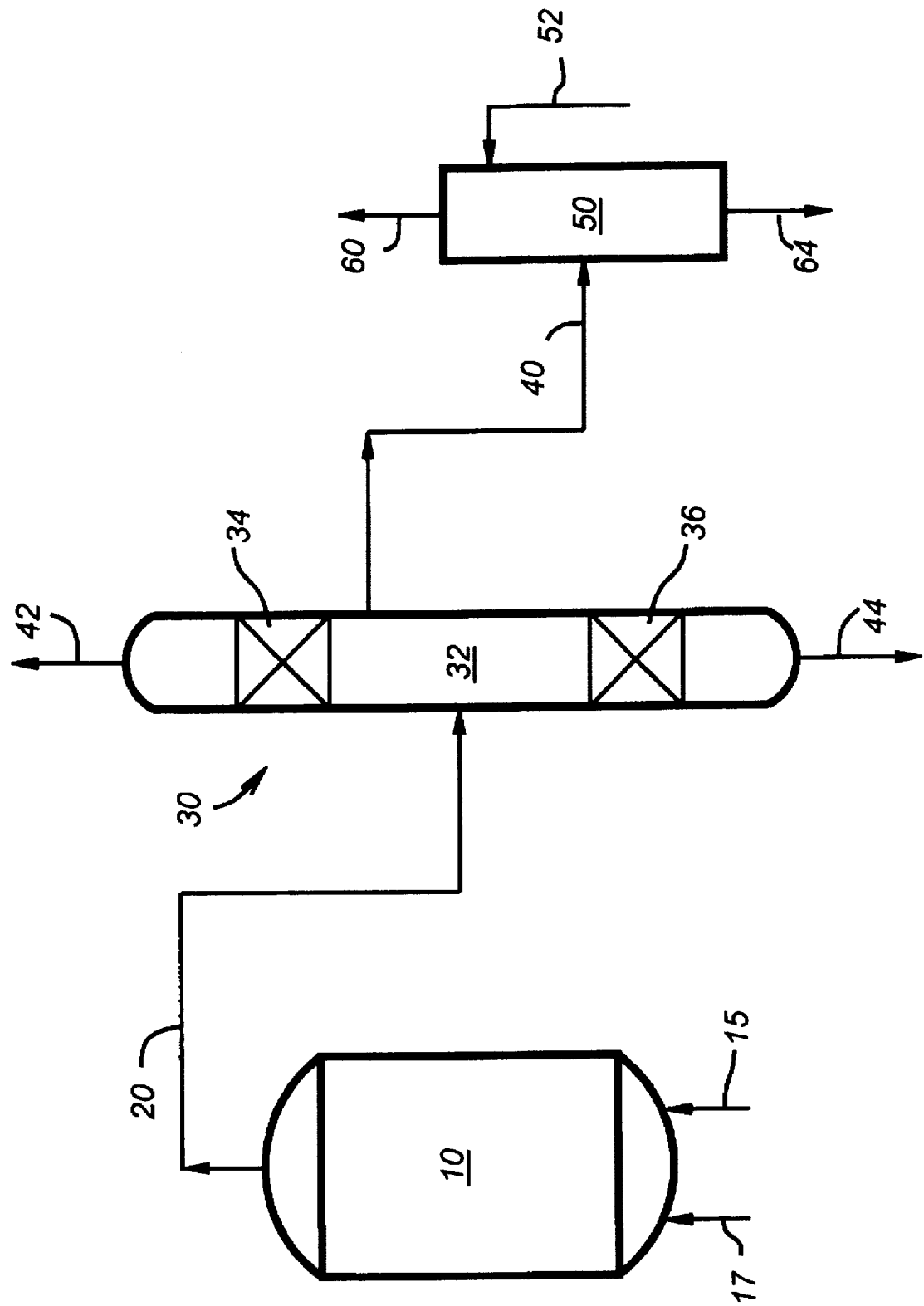

MANUFACTURE OF METHYL TERTIARY BUTYL ETHER IN REACTIVE DISTILLATION COLUMN

BACKGROUND OF THE INVENTION

1. Technical Field of the Invention

This invention relates to a process for the manufacture of methyl tertiary butyl ether (MTBE) from tertiary butyl alcohol (TBA) and methanol (MeOH) wherein a primary reaction product is formed comprising MTBE, unreacted MeOH, unreacted TBA, isobutylene (IBTE), water and oxygen-containing by-products and wherein the primary reaction product is charged to a reactive distillation column where additional MTBE is prepared from the unreacted MeOH, unreacted TBA, and isobutylene.

More particularly, this invention relates to a process for the manufacture of methyl tertiary butyl ether (MTBE) from tertiary butyl alcohol (TBA) and methanol (MeOH) wherein a primary reaction product is formed comprising MTBE, unreacted MeOH, unreacted TBA, isobutylene, water and oxygen-containing by-products and wherein the primary reaction product is charged to a reactive distillation column where additional MTBE is prepared from the unreacted MeOH, unreacted TBA, isobutylene and wherein a lower boiling fraction comprising IBTE, MEOH and oxygen-containing by-products, an intermediate boiling fraction comprising MTBE and MeOH and a higher boiling fraction comprising TBA, MeOH and water and wherein the intermediate boiling fraction is washed with water to separate the intermediate boiling fraction into a supernatant MTBE extract and a raffinate comprising water and methanol.

2. Prior Art

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

Kruse et al. U.S. Pat. No. 5,243,091 discloses a method for the preparation of methyl tertiary butyl ether wherein a mixture of methanol and tertiary butyl alcohol is catalytically reacted to form a reaction product that is separated into a first lower boiling (lighter) distillation fraction comprising isobutylene, methanol and methyl tertiary butyl ether and a first higher boiling (heavier) distillation fraction comprising methanol, tertiary butyl alcohol and water. The first higher boiling distillation fraction is distilled to provide a second lower boiling TBA fraction for recycle. The first lower boiling distillation fraction and isobutylene are reacted in a finishing reactor to form a finishing reactor conversion product that is charged to a methanol extraction zone and countercurrently contacted with water to provide an overhead extract comprising MTBE, water and isobutylene, from which the isobutylene is recovered for recycle.

Gupta U.S. Pat. No. 5,292,964 discloses a method for the preparation of methyl tertiary butyl alcohol wherein a mixture of methanol and tertiary butyl alcohol are catalytically reacted to forms reaction product containing the water of etherification and at least one mol of methanol per two moles of methyl tertiary butyl ether, wherein the reaction product is fractionated to separate a lower boiling methanol and methyl tertiary butyl ether fraction from the water and tertiary butyl alcohol and wherein the methanol in the lower boiling distillation fraction is reacted with isobutylene to form additional methyl tertiary butyl ether.

Gupta states that it is essential to provide a reaction product containing at least one mol of methanol per two moles of methyl tertiary butyl ether, so that water is separable from the methyl tertiary butyl ether in the fractionating column to provide a lower boiling distillation fraction substantially free from water.

Smith U.S. Pat. No. 4,215,011 discloses a reactive distillation column having both a catalytic function and a distillation function that is useful, for example, in the polymerization of butene.

In Smith U.S. Pat. No. 4,232,177 a method for conducting chemical reactions in a reactive distillation column is disclosed wherein a reaction mixture is fed to a reactive distillation column and contacted with a fixed bed catalytic packing to concurrently carry out the reaction and to fractionate the reaction mixture.

Various types of catalytic packing that can be used in a reactive distillation column are disclosed in Smith U.S. Pat. No. 4,443,559.

Smith U.S. Pat. No. 5,118,873 discloses a process wherein isobutylene and methanol are reacted in the presence of an acid cation exchange resin to form MTBE and concurrently fractionated to provide an overhead fraction comprising unreacted isobutylene and unreacted methanol and a bottoms fraction comprising methyl tertiary butyl ether and contaminants.

In copending Kruse et al. U.S. patent application entitled "Method for the Reduced Formation of Tertiary Butyl Alcohol in a Finishing Reactor in the Manufacture of Methyl Tertiary Butyl Ether" (Docket No. 81,256) a process is disclosed for the preparation of methyl tertiary butyl ether wherein a mixture of methanol and tertiary butyl alcohol are catalytically reacted to form a reaction product comprising unreacted methanol, unreacted tertiary butyl alcohol, water, isobutylene and methyl tertiary butyl ether; the reaction product being separated into a substantially anhydrous first lower boiling distillation fraction comprising isobutylene, methanol and methyl tertiary butyl ether and a second higher boiling distillation fraction comprising methanol, tertiary butyl alcohol and water, and the isobutylene and methanol in the first lower boiling distillation fraction are reacted in a finishing reactor to form an isobutylene conversion product that contains additional methyl tertiary butyl ether and that is substantially free from tertiary butyl alcohol.

SUMMARY OF THE INVENTION

This invention relates to an improvement in a process for the manufacture of MTBE from TBA and MeOH wherein tertiary butyl alcohol and methanol are reacted in a primary reactor in the presence of an acid cation exchange resin to provide a primary reaction product comprising methyl tertiary butyl ether, unreacted tertiary butyl alcohol, unreacted methanol, isobutylene, water and oxygen-containing by-products and wherein the primary reaction product is charged to a reactive distillation column where additional MTBE is prepared from the unreacted MeOH, unreacted TBA, and isobutylene and wherein the reaction products are distilled to provide a lower boiling fraction comprising oxygen-containing by-products, an intermediate fraction comprising MTBE and MeOH and a higher boiling fraction comprising water.

More particularly, this invention relates to an improvement in a process for the manufacture of MTBE from TBA and MeOH wherein tertiary butyl alcohol and methanol are reacted in a primary reactor in the presence of an acid cation exchange resin to provide a primary reaction product comprising methyl tertiary butyl ether, unreacted tertiary butyl alcohol, unreacted methanol, isobutylene, water and oxygen-containing by-products and wherein the primary reaction product is charged to the intermediate section of an extractive distillation column having an upper reactive distillation section above the primary reaction product charge point and a lower reactive distillation section below the primary reaction product charge point, wherein additional MTBE is prepared from IBTE and MeOH in the upper reactive distillation section, wherein additional MTBE is prepared from TBA and MeOH in the lower reactive distillation section, wherein an intermediate boiling fraction comprising additional MTBE and unreacted MeOH is recovered from the reactive distillation column, wherein a lower boiling fraction comprising oxygen-containing byproducts is recovered from the reactive distillation column and wherein a higher boiling fraction comprising water is recovered from the reactive distillation column.

The intermediate boiling fraction is suitably washed with water to separate the intermediate boiling fraction into a supernatant MTBE extract and a raffinate comprising water and methanol from which methanol can be recovered for recycle.

In greater detail, this invention relates to an improvement in a process for the manufacture of MTBE from TBA and MeOH which comprises:

a) continuously passing a feed mixture comprising TBA and MeOH through a primary MTBE reactor containing a bed of a TBA/MeOH etherification catalyst under etherification reaction conditions to form an etherification reaction product comprising unreacted MeOH, unreacted TBA, water, isobutylene (IBTE) and MTBE, b) continuously passing the primary reaction product to the intermediate section of an extractive distillation column having an upper reactive distillation section above the primary reaction product charge point and a lower reactive distillation section below the primary reaction product charge point, c) continuously separating the primary reaction product in the intermediate distillation section of the reactive distillation column into a lower boiling fraction comprising isobutylene, methanol and oxygen-containing byproducts, an intermediate boiling fraction comprising MTBE and MeOH and a higher boiling fraction comprising TBA, MeOH and water, d) continuously recovering the intermediate boiling fraction, e) continuously passing the lower boiling fraction through the upper reactive distillation section to convert the IBTE and MeOH contained therein into additional MTBE and water for downflow into the intermediate distillation section, f) continuously recovering the remaining portion of the lower boiling fraction adjacent the top of the reactive distillation column, g) continuously passing the higher boiling fraction through the lower reactive distillation section to convert the TBA and MeOH contained therein into additional MTBE for upflow to the intermediate section and for recovery of a higher boiling water fraction adjacent the bottom of the extractive distillation column.

In accordance with a preferred embodiment of the present invention, the intermediate boiling fraction is continuously charged to a methanol solvent extraction zone and countercurrently contacting therein with water to provide an overhead extract comprising MTBE and a raffinate comprising MeOH and contaminating quantities of water and oxygen-containing by-products.

DETAILED DESCRIPTION OF THE PRESENT INVENTION

The Etherification Reaction Catalyst

In accordance with the MTBE manufacture and purification method of the present invention, a primary etherification reactor containing a bed of etherification catalyst is utilized. A wide variety of etherification catalysts can be used for this purpose, such as supported phosphorus acid-type catalysts. A preferred catalyst is an acid cation exchange resin such as an acidic ion exchange resin consisting essentially of sulfonated polystyrene, for example, a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalysts of this nature is disclosed, for example, in Rao U.S. Pat. No. 4,144,138.

Also, Kieselguhr impregnated with phosphoric acid is disclosed in Frolich U.S. Pat. No. 2,282,469 and titania having phosphoric acid impregnated thereon is disclosed in Knifton U.S. Pat. No. 4,822,921. A hereto polyacid such as 12-tungstophosphoric acid or 12-molybdophosphoric acid supported on titania, etc., may be used.

Zeolites as disclosed in Japanese Patent 0007432 or aluminosilicate zeolites as disclosed in Chang et al. U.S. Pat. No. 4,058,576 may also be used.

The reaction conditions to be utilized when reacting methanol with tertiary butyl alcohol in the presence of a sulfonic acid resin etherification catalyst include a reaction temperature of about 90° to about 140° C., a pressure of about 30 to about 500 psia and a space velocity of about 0.5 to about 20 volumes of feed per volume of etherification catalyst per hour.

The Reactive Distillation Column

The reactive distillation column to be used in accordance with the present invention is a reactive distillation column of the type disclosed in the Smith patents referenced above. The reactive distillation column of the present invention will comprise an intermediate or central distillation section to which the primary reaction product is charged for processing.

The intermediate section is operated so as to separate the primary reaction product into an intermediate boiling fraction comprising MTBE and MeOH, a lower boiling fraction comprising IBTE, MeOH and lower boiling oxygen-containing impurities and higher boiling fraction comprising TBA, MeOH and higher boiling oxygen-containing impurities.

The intermediate boiling fraction comprising MTBE and MeOH is recovered from the intermediate section of the extractive distillation column as an intermediate product fraction.

The reactive distillation column of the present invention is provided with an upper reactive distillation section and a lower reactive distillation section. Each of the reactive distillation sections will contain a packing comprising a solid resin etherification catalyst of the type disclosed by the Smith patents. Any suitable solid resin etherification catalyst may be used in the reactive distillation sections, such as an acidic ion exchange resin consisting essentially of sulfonated polystyrene, for example, a sulfonated divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

The lower boiling fraction includes IBTE, MeOH and lower boiling oxygen-containing impurities and flows upwardly from the intermediate distillation section through the upper reactive distillation section where the IBTE and MeOH contained therein are converted into additional MTBE and water for downflow into the intermediate distillation section. The remaining portion of the lower boiling fraction is recovered adjacent the top of the reactive distillation column.

The higher boiling fraction comprising TBA, MeOH and higher boiling oxygen-containing impurities flows downwardly from the intermediate distillation section through the lower reactive distillation section where the TBA and MeOH contained therein are converted into additional MTBE for upflow to the intermediate section and water for recovery with downflowing water adjacent the bottom of the extractive distillation column.

Operating conditions in the upper and lower reactive distillation sections include, for example, a temperature of about 35° to about 130° C., and a pressure of about 30 to about 500 psia.

BRIEF DESCRIPTION OF THE DRAWING

The drawing is a schematic flow sheet with conventional parts omitted showing the general reaction and recovery sequence of the present invention for the manufacture of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reactor 10 containing a bed of solid etherification catalyst.

A substantially peroxides-free tertiary butyl alcohol feed stream is continuously charged by a charge line 17. Methanol is continuously charged to the primary reactor 10 by a line 15. The flow of methanol and tertiary butyl alcohol to the primary reactor 10 is regulated so that a molar excess of methanol is present, such as, for example, a molar ratio of about 1.1 to about 3 moles of methanol per mol of tertiary butyl alcohol.

Within the primary reactor 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the primary reaction zone 10 is suitably such that about 0.5 to about 20 volumes of feed mixture per volume of etherification catalyst per hour are fed to the etherification reaction zone 10. More preferably, a feed ratio of from about 1 to about 4 volumes of feed mixture per volume of etherification catalyst per hour is used.

Within the primary reactor 10, methanol will react with the tertiary butyl alcohol to form methyl tertiary butyl ether and water which will be contained in a primary reaction product discharged from the primary reactor 10 by way of a line 20 leading to a reactive distillation column 30. By-product isobutylene will also be formed.

As a specific example, when the solid etherification catalyst is a sulfonic acid resin such as Amberlyst 15 and when the molar ratio of methanol to tertiary butyl alcohol in the feed mixture charged to the primary reactor 10 is a ratio of about 2.0 moles of methanol per mole of tertiary butyl alcohol, and the reaction is conducted at a temperature of about 100° C. at a feed rate of about 2.0 volumes of feed mixture per volume of catalyst per hour, the primary etherification reaction product will typically have the composition in part shown by the following table:

| Component | % |
|---|---|
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, and any ditertiary butyl peroxide, tertiary butyl formate, etc., initially present in the tertiary butyl alcohol feedstock.

The primary etherification reaction product is charged by a line 20 to a reactive distillation column 30 comprising an intermediate distillation section 32, an upper reactive distillation section 34 and a lower distillation section 36. Within the reactive distillation column 30, the primary etherification reaction product is fractionated under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation conditions being selected such that substantially all of the MTBE and co-distilling MeOH in the etherification reaction product 20 exit the reactive distillation column 30 through intermediate draw-off line 40.

The lower boiling components including IBTE, MeOH and lower boiling oxygen-containing impurities flow upwardly from the intermediate distillation section 32 through the upper reactive distillation section 34 where the IBTE and MeOH contained therein are converted into additional MTBE and water for downflow into the intermediate distillation section 32. The remaining portion of the lower boiling fraction exits the reactive distillation column by a discharge line 42 adjacent the top of the reactive distillation column 30.

The higher boiling components, which comprise TBA, MeOH and higher boiling oxygen-containing impurities flow downwardly from the inter-mediate distillation section 32 through the lower reactive distillation section 36 where the TBA and MeOH contained therein are converted into additional MTBE for upflow to the intermediate section 32 and water which exits the reactive distillation column adjacent the bottom of the extractive distillation column by a lower discharge line 44. The intermediate distillation fraction is discharged from the reactive distillation column by a line 40 leading to a methanol solvent extraction zone 50 where it is countercurrently contacted with water introduced into the solvent extraction zone 50 by a charge line 52.

Within the methanol solvent extraction zone 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extraction conditions may suitably include a temperature of about 20° to about 60° C., and more preferably from about 30° to about 40° C., and a pressure of about 50 to about 500 psia, and more preferably from about 50 to about 150 psia.

As a consequence, a supernatant extract comprising MTBE will be formed which is withdrawn from the methanol solvent extraction zone 50 by line 60. The raffinate, comprising methanol, water and oxygen-containing impurities is discharged from the solvent extraction zone 50 byway of a bottoms charge line 64.

What is claimed is:

1. A method for the manufacture of MTBE from TBA and MeOH which comprises:

reacting tertiary butyl alcohol and methanol in a primary reactor in the presence of an acid cation exchange resin to provide a primary reaction product comprising methyl tertiary butyl ether, unreacted tertiary butyl alcohol, unreacted methanol, isobutylene, water and oxygen-containing by-products, charging the primary reaction product to a reactive distillation column comprising an intermediate distillation section, an upper reactive distillation section above the primary reaction product charge point and a lower reactive distillation section below the primary reaction product charge point, separating said primary reaction product in said intermediate distillation section into a lower boiling fraction comprising isobutylene and methanol, an intermediate fraction comprising MTBE and methanol and a higher boiling fraction comprising tertiary butyl alcohol, methanol and water, flowing said lower boiling fraction upwardly from said intermediate distillation section into said upper reactive distillation section and reacting isobutylene with methanol therein to provide additional MTBE for downflow into said intermediate distillation section, flowing said higher boiling fraction downwardly from said intermediate distillation section into said lower reactive distillation section and reacting tertiary butyl alcohol with methanol therein to provide additional MTBE for upflow into said intermediate distillation section, and recovering said intermediate fraction from said intermediate distillation section.

2. A method as in claim 1 wherein the acid cation exchange resin comprises a sulfonated divinyl benzene cross-linked polystyrene matrix containing from about 0.5 to about 20% of copolymerized divinyl benzene.

3. A method as in claim 1 wherein the reaction conditions include a reaction temperature of about 90° to about 140° C., a pressure of about 30 to about 500 psia and a space velocity of about 0.5 to about 20 volumes of feed per volume of etherification catalyst per hour.

4. A method as in claim 1 wherein the intermediate boiling fraction is washed with water in a methanol extraction zone to separate the intermediate boiling fraction into a supernatant MTBE extract and a raffinate comprising water and methanol.

5. A method for the manufacture of MTBE from TBA and MeOH which comprises:

a) continuously passing a feed mixture comprising TBA and MeOH through a primary MTBE reactor containing a bed of a TBA/MeOH etherification catalyst under etherification reaction conditions to form an etherification reaction product comprising unreacted MeOH, unreacted TBA, water, isobutylene (IBTE) and MTBE, b) continuously passing the primary reaction product to the intermediate distillation section of a reactive distillation column having an upper reactive distillation section above the intermediate section and a lower reactive distillation section below the intermediate section, c) continuously separating the primary reaction product in the intermediate distillation section of the reactive distillation column into a lower boiling fraction comprising isobutylene, methanol and oxygen-containing by-products, an intermediate boiling fraction comprising MTBE and MeOH and a higher boiling fraction comprising TBA, MeOH and water, d) continuously recovering the intermediate boiling fraction, e) continuously passing the lower boiling fraction through the upper reactive distillation section to convert the IBTE and MeOH contained therein into additional MTBE and water for downflow into the intermediate distillation section, f) continuously recovering the remaining portion of the lower boiling fraction adjacent the top of the reactive distillation column, and g) continuously passing the higher boiling fraction through the lower reactive distillation section to convert the TBA and MeOH contained therein into additional MTBE for upflow to the intermediate section and for recovery of a higher boiling water fraction adjacent the bottom of the extractive distillation column.

6. A method as in claim 5 wherein the acid cation exchange resin comprises a sulfonated divinyl benzene cross-linked polystyrene matrix containing from about 0.5 to about 20% of copolymerized divinyl benzene.

7. A method as in claim 5 wherein the reaction conditions include a reaction temperature of about 90° to about 140° C., a pressure of about 30 to about 500 psia and a space velocity of about 0.5 to about 20 volumes of feed per volume of etherification catalyst per hour.

8. A method as in claim 5 wherein the intermediate boiling fraction is washed with water in a methanol extraction zone to separate the intermediate boiling fraction into a supernatant MTBE extract and a raffinate comprising water and methanol.

* * * * *